US010532350B2

(12) United States Patent
Zhang et al.

(10) Patent No.: US 10,532,350 B2
(45) Date of Patent: *Jan. 14, 2020

(54) METHOD FOR SYNTHESIZING SILICOALUMINOPHOSPHATE-34 MOLECULAR SIEVES USING MONOISOPROPANOLAMINE

(71) Applicant: W. R. Grace & Co.-Conn., Columbia, MD (US)

(72) Inventors: Qiuhua Zhang, Columbia, MD (US); Manoj Koranne, Clarksville, MD (US)

(73) Assignee: W.R. GRACE & CO.-CONN, Colombia, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/504,715

(22) PCT Filed: Aug. 21, 2015

(86) PCT No.: PCT/US2015/046212
§ 371 (c)(1),
(2) Date: Feb. 17, 2017

(87) PCT Pub. No.: WO2016/029076
PCT Pub. Date: Feb. 25, 2016

(65) Prior Publication Data
US 2017/0239649 A1    Aug. 24, 2017

Related U.S. Application Data

(60) Provisional application No. 62/040,538, filed on Aug. 22, 2014.

(51) Int. Cl.
*C01B 39/54* (2006.01)
*B01J 29/85* (2006.01)
(Continued)

(52) U.S. Cl.
CPC ............ *B01J 29/85* (2013.01); *B01J 37/009* (2013.01); *B01J 37/0018* (2013.01); *B01J 37/04* (2013.01);
(Continued)

(58) Field of Classification Search
CPC ....... C01B 39/54; B01J 29/85; B01J 29/7015; C07C 1/20; C07C 2529/85
See application file for complete search history.

(56) References Cited

U.S. PATENT DOCUMENTS

| | | | |
|---|---|---|---|
| 4,310,440 A | 1/1982 | Wilson et al. | 252/435 |
| 4,440,871 A * | 4/1984 | Lok | B01J 20/18 208/114 |

(Continued)

FOREIGN PATENT DOCUMENTS

| | | | |
|---|---|---|---|
| CN | 101531377 | 9/2009 | C01B 39/54 |
| CN | 101555024 | 10/2009 | C01B 39/54 |

(Continued)

OTHER PUBLICATIONS

Anthony, Rayford G., "Methanol to Olefins: Enhancing Selectivity to Ethylene and Propylene Using SAPO-34 and Modified SAPO-34". Periodical: Texas A&M University, Dissertation / Thesis No. 3113303 (2001).

(Continued)

*Primary Examiner* — David M Brunsman
(74) *Attorney, Agent, or Firm* — Charles A. Cross; Beverly J. Artale (57) ABSTRACT

A method for synthesizing small crystals of silicoaluminophosphate-34 (SAPO-34) molecular sieves with high structural purity. The method includes first forming a slurry comprising monoisopropanolamine. Then, the slurry is aged to form an aged slurry. Finally, crystallization of silicoalu- (Continued)

minophosphate molecular sieves comprising the SAPO-34 molecular sieves is induced from the aged slurry.

16 Claims, 4 Drawing Sheets

(51) Int. Cl.
- *B01J 37/00* (2006.01)
- *B01J 37/04* (2006.01)
- *B01J 37/06* (2006.01)
- *B01J 37/08* (2006.01)
- *B01J 37/10* (2006.01)
- *C07C 1/20* (2006.01)
- *B01J 29/70* (2006.01)

(52) U.S. Cl.
CPC .............. *B01J 37/06* (2013.01); *B01J 37/08* (2013.01); *B01J 37/10* (2013.01); *C01B 39/54* (2013.01); *C07C 1/20* (2013.01); *B01J 29/7015* (2013.01); *C07C 2529/85* (2013.01)

(56) References Cited

U.S. PATENT DOCUMENTS

| | | | |
|---|---|---|---|
| 4,499,327 A | 2/1985 | Kaiser et al. | |
| 4,677,243 A | 6/1987 | Kaiser et al. | 585/638 |
| 4,861,743 A | 8/1989 | Flank et al. | 502/214 |
| 5,609,843 A | 3/1997 | Wendelbo et al. | 423/306 |
| 5,663,471 A | 9/1997 | Kvisle et al. | 585/639 |
| 6,334,994 B1 | 1/2002 | Wendelbo et al. | 423/718 |
| 6,540,970 B1 | 4/2003 | Strohmaier et al. | 423/306 |
| 6,620,983 B1 | 9/2003 | Cao et al. | 585/640 |
| 6,767,858 B1 | 7/2004 | Coa et al. | 502/214 |
| 7,112,316 B1 | 9/2006 | Konrad et al. | 423/709 |
| 7,309,679 B2 | 12/2007 | Karch et al. | 502/208 |
| 7,341,706 B2 | 3/2008 | Fuglerud et al. | 423/702 |
| 7,341,707 B2 | 3/2008 | Fuglerud et al. | 423/702 |
| 7,375,050 B2 | 5/2008 | Mertens et al. | 502/214 |
| 7,807,122 B2 | 10/2010 | Mertens et al. | 423/306 |
| 7,977,273 B2 | 7/2011 | Sinkler et al. | 502/214 |
| 8,617,474 B2 * | 12/2013 | Bull | B01D 53/9418 422/171 |
| 8,679,227 B2 | 3/2014 | Falconer et al. | 95/51 |
| 9,744,526 B2 * | 8/2017 | Tian | C07C 1/20 |
| 9,889,440 B2 * | 2/2018 | Zhang | B01J 29/85 |
| 2006/0292053 A1 | 12/2006 | Mertens et al. | 423/306 |
| 2009/0062113 A1 | 3/2009 | Miller et al. | 502/210 |
| 2010/0022722 A1 | 1/2010 | Mertens et al. | 526/75 |
| 2010/0310440 A1 | 12/2010 | Bull et al. | 423/239.1 |
| 2012/0203046 A1 | 8/2012 | Chae et al. | 585/638 |
| 2012/0251422 A1 | 10/2012 | Li et al. | 423/239.1 |

FOREIGN PATENT DOCUMENTS

| | | | |
|---|---|---|---|
| CN | 101555024 A * | 10/2009 | |
| CN | 101767800 A * | 7/2010 | |
| CN | 101481122 | 3/2011 | B01J 29/85 |
| CN | 101767800 | 11/2011 | C01B 39/54 |
| CN | 101612592 | 12/2011 | B01J 35/08 |
| CN | 101525141 | 2/2012 | C01B 39/54 |
| CN | 102336412 A * | 2/2012 | |
| CN | 102424399 A | 4/2012 | |
| CN | 102389833 | 12/2012 | Y02P 20/52 |
| CN | 102336412 | 3/2013 | C01B 39/54 |
| CN | 103130241 | 5/2015 | C01B 39/54 |
| CN | 105036153 A * | 11/2015 | |
| EP | 0293919 | 12/1988 | C01B 25/45 |
| EP | 1142833 | 10/2001 | C01B 37/06 |
| EP | 0993867 | 2/2005 | B01J 29/85 |
| EP | 2269733 | 1/2011 | B01J 29/00 |
| JP | 2000246111 | 9/2000 | B01J 29/06 |
| JP | 2000246111 A | 9/2000 | |
| KR | 1020090028018 | 3/2009 | B01J 29/85 |
| WO | 2013106571 | 7/2013 | B01J 29/04 |
| WO | 2013159828 | 10/2013 | B01J 29/85 |
| WO | 2014089736 | 6/2014 | C01B 39/54 |
| WO | 2014089738 | 6/2014 | C01B 39/54 |
| WO | 2014089740 | 6/2014 | C01B 39/54 |
| WO | 2015061544 A1 | 4/2015 | |

OTHER PUBLICATIONS

Chae, Ho-Jeong; Park, In-Jung; Song, Young-Ha; Jeong, Kwang-Eun; Kim, Chul-Ung; Shin, Chae-Ho; Jeong, Soon-Yong, "Physicochemical Characteristics of SAPO-34 Molecular Sieves Synthesized with Mixed Templates as MTO Catalysts". Ho; Jeong, Soon-Yong; Periodical: Journal of Nanoscience and Nanotechnology, v 10, n 1, p. 195-202(8) (2010).

Chen, De; Moljord, Kjell; Fuglerud, Terje; Holmen, Anders "The Effect of Crystal Size of SAPO-34 on the Selectivity and Deactiviation of the MTO Reaction", Department of Industrial Chemistry, Norwegian University of Science and Technology, N-7034 Trondheim, Norway; Microporous and Mesoporous Materials 29, 191-203 (1999).

Pastore, Heloise; Coluccia, Salvatore; Marchese, Leonardo, "Porous Aluminophosphates: from Molecular Sieves to Designed Acid Catalysts", Periodical: Annual Review of Materials Research, v 35, n 51, p. 351-395, (2005).

Tan, Juan; Liu, Zhongmin; Bao, Xinhe; Liu, Xianchun; Han, Xiuwen; He, Changqing; Zhai, Runsheng "Crystallization and Si Incorporation Mechanisms of SAPO-34", State Key Laboratory of Catalysis, Dalian Institute of Chemical Physics, Chinese Academy of Science, Dalian 116023; Microporous and Mesoporous Materials 53, p. 97-108 (2002).

Wang, Dehua; Tian, Peng; Yang, Miao; Xu, Shutao; Fan, Dong; Su, Xiang; Yang, Yue; Wang, Chan; Liu, Zhongmin "Synthesis of SAPO-34 with Alkanolamines as Novel Templates and Their Application for CO2 Separation" Microporous and Mesopourous Materials 194, 8-14, (2014).

Wilson, Stephen; Barger, Paul, "The Characteristics of SAPO-34 Which Influence the Conversion of Methanol to Light Olefins"; Micopourous and Mesoporous Materials 29, 117-126 (1999).

Yang, S.M.; Wang, S.I.; Huang, C.S., "Methanol Conversion on Silicoaluminophosphate Molecular Sieves"; Periodical: Studies in Surface Science and Catalysis, v 61, p. 429-435 (1991).

PCT Search Report and Written Opinion for PCT/US2015/46212; dated Nov. 27, 2015.

* cited by examiner

METHOD FOR SYNTHESIZING SILICOALUMINOPHOSPHATE-34 MOLECULAR SIEVES USING MONOISOPROPANOLAMINE

CROSS REFERENCE TO RELATED APPLICATION

This application claims the benefit of the filing date of U.S. Provisional Patent Application No. 62/040,538 filed Aug. 22, 2014, which is hereby incorporated by reference.

FIELD OF THE INVENTION

This invention relates to silicoaluminophosphate-34 (SAPO-34) molecular sieves, and more particularly to a method for synthesizing SAPO-34 molecular sieves using monoisopropanolamine.

BACKGROUND

Silicoaluminophospate (SAPO) is a class of materials having a microporous crystal framework structure of $PO_2^+$, $AlO_2^-$, and $SiO_2$ tetrahedral units, and whose essential empirical chemical composition in the as-synthesized form and on an anhydrous basis can be represented as follows:

$$mR:(Si_xAl_yP_z)O_2$$

wherein "R" represents at least one organic structure directing agent present in the intracrystalline pore system; "m" represents the moles of "R" present per mole of $(Si_xAl_yP_z)O_2$; and "x," "y," and "z" represent respectively the mole fractions of silicon, aluminium, and phosphorus present in the oxide moiety.

Light olefins are traditionally produced from hydrocarbon feed stocks via thermal cracking of natural gas liquids or petroleum based naphtha and/or fluid catalytic cracking (FCC) of petroleum based feedstocks. With the increasing demand of light olefins, especially ethylene and propylene, alternate routes have been widely explored. Catalytic conversion of alcohols such as methanol to light olefins on molecular sieves is one of the most promising alternative routes to produce ethylene and propylene. This is especially true because methanol may be made from syngas derived from coal, methane, or biomass.

Catalytic conversion of methanol (and other light alcohols) to light olefins using microporous crystallite SAPO molecular sieves has been described by Kaiser (U.S. Pat. No. 4,499,327). The crystal structure, the silicon content and distribution, and the crystal size of the SAPO molecular sieves are among important features of the SAPO molecular sieves for maximizing the selectivity of catalytic conversion to light olefins.

There are a number of different structures of SAPOs which are represented by different framework types. These SAPOs include SAPO-5, SAPO-11, SAPO-18, SAPO-34, SAPO-35, SAPO-41, and SAPO-56. Of these structures, SAPOs represented by framework type CHA (as described in Atlas of Zeolite Framework Types, 2007, 6th Edition, page 96) are known to be selective for the methanol-to-olefins (MTO) reaction (Kaiser, U.S. Pat. No. 4,499,327). In particular, SAPO-34, a CHA framework type with a pore opening of about 4 Å and cylindrical cages within the structure of about 10×6.7 Å, is highly selective for the MTO reaction. However, the presence of other SAPOs such as SAPO-5 or SAPO-11 with SAPO-34 tends to produce undesired products (Stud. Surf. Sci. Catal., 61, 429 (1991). Hence, it is very important to produce SAPO-34 molecular sieves with high structural purity for the MTO reaction.

Furthermore, SAPO-34 molecular sieves with low silicon content and uniform distribution are important for maximizing the selectivity to light olefins in the MTO reaction (Microporous and Mesoporous Materials, 29, 117-126 (1999); Microporous and Mesoporous Materials 53, 97-108 (2002)). Small crystals of SAPO-34 molecular sieves are important to reduce undesired coke formation and improve lifetime of the catalyst (Microporous and Mesoporous Materials 29, 191-203 (1999)). Moreover, features such as flammability, boiling point, toxicity, and amount of the structure directing agent as well as filterability and yields of solid SAPOs recovered during the synthesis have important practical implications for commercial production of SAPO-34 molecular sieves.

During the synthesis of SAPOs, structure directing agents, which are also called templates, are typically used to direct the formation of particular types of framework structures. However, the structure directing agents' effect on the final crystalline structure of SAPOs varies. Lok et al describe the synthesis of SAPO-34 molecular sieves (along with other SAPO structures) with respect to various structure directing agents and synthesis conditions in U.S. Pat. No. 4,440,871. While certain structure directing agents direct or initiate formation of SAPO-34, other crystalline structures such as SAPO-5 are also formed during the synthesis.

Furthermore, those structure directing agents that are currently known to be more specific for making SAPO-34, such as tetraethylammonium hydroxide (TEAOH), diethylamine (DEA), triethylamine (TEA), or morpholine, have other practical implications. For example, Juan Tan et al discloses that TEA may be used to manufacture small crystal sizes of SAPO-34 (Microporous and Mesoporous Materials, 53 97-108, 2002). However, TEA is volatile, toxic, and relatively noxious, and therefore it is more desirable to use environmentally benign alternatives in the commercial production of SAPO-34.

U.S. Pat. No. 4,677,243 discloses a method for synthesizing SAPO-34 using tetraethylammonium hydroxide (TEAOH) as a structure directing agent. However, TEAOH is an expensive chemical which limits its practical use in the commercial production of SAPO-34.

US 2012/0203046 A1 also discloses a method for synthesizing SAPO-34 using two structure directing agents, TEAOH and DEA. However, no experimental data is disclosed regarding the structural purity of the solid product separated from the slurry comprising crystallized SAPO-34. Moreover, DEA is volatile, toxic, and relatively noxious, and therefore difficult to use in the commercial production of SAPO-34.

Alkanolamines (also named aminoalcohols) are desirable structure directing agents because they have high boiling points, high flashpoints and are relatively less toxic. However, so far, the disclosed synthesis methods using alkanolamines as structure directing agents do not produce SAPO-34 or produce SAPO-34 with low structural purity, low yield, or high usage of alkanolamine templates. For example, Chae et al disclose using N,N-diethanolamine to form SAPO-5, an AF1 type of structure. (Journal of Nanoscience and Nanotechnology, 10, 195-202, 2010), U.S. Pat. No. 4,310,440 describes that AIPO-5, an analogue of SAPO-5, is prepared using triethanolamine, N,N-dimethylethanolamine, N,N-diethylethanolamine, N-methyldiethanolamine, and N-methylethanolamine as structure directing agents. However, there is no mention of synthesis of SAPO-34.

U.S. Pat. No. 6,767,858 discloses a method of synthesizing SAPO-34 using N-methylethanolamine as a structure directing agent at a temperature of 170° C. for 20 hours to 14 days with a SAPO-34 yield of 4.2%. The SAPO-34 yield increases to 27.1% when $HPF_6$ is added as the fluorine source for the synthesis.

WO2014/089736 describes that SAPO-34 is synthesized using diisopropanolamine (DiPA) as a templating agent. The molar ratio of diisopropanolamine to alumina ($DiPA/Al_2O_3$) is 5 or higher. The high usage of templating agent is not economical for commercial production.

WO2014/089738A1 describes a method of synthesizing SAPO-34 using N-methyldiethanolamine as a templating agent. WO2014/089740A1 describes a method of synthesizing SAPO-34 using diglycolamine as a templating agent. However, the structural purity or yield of the final products is not disclosed.

European patent application No. 0993,867 discloses that SAPO-34 may be prepared using diethanolamine at 200° C. for 60 hours. However, no purity, yield, or physical properties are disclosed. It is also noted that this patent application discloses making SAPO-5 from the same components and the same method by just using different amounts of diethanolamine. In addition, there are no details provided on structural purity or yield of SAPO-5.

BRIEF SUMMARY

Accordingly, one example of the present invention is a method for synthesizing silicoaluminophosphate-34 (SAPO-34) molecular sieves using monoisopropanolamine as a structure directing agent.

The method comprises first forming a slurry comprising monoisopropanolamine. The slurry may include a source of phosphorus, a source of aluminium, and a source of silicon. Then, the slurry is aged to form an aged slurry. Finally, crystallization of SAPO molecular sieves comprising the SAPO-34 molecular sieves is induced from the aged slurry under hydrothermal conditions.

Another example of the present invention is SAPO-34 molecular sieves which have a chemical composition described on an anhydrous basis as $mR:(Si_x.Al_y.P_z)O_2$, wherein m is in the range of 0.01 to 0.3, x in the range of 0.01 to 0.3, y in the range of 0.3 to 0.6, and z in the range of 0.3 to 0.6.

DETAILED DESCRIPTION

The present invention is described with reference to embodiments of the invention. Throughout the description of the invention, reference is made to FIGS. 1 to 3. When referring to the figures, like elements shown throughout are indicated with like reference numerals.

Figure 1:
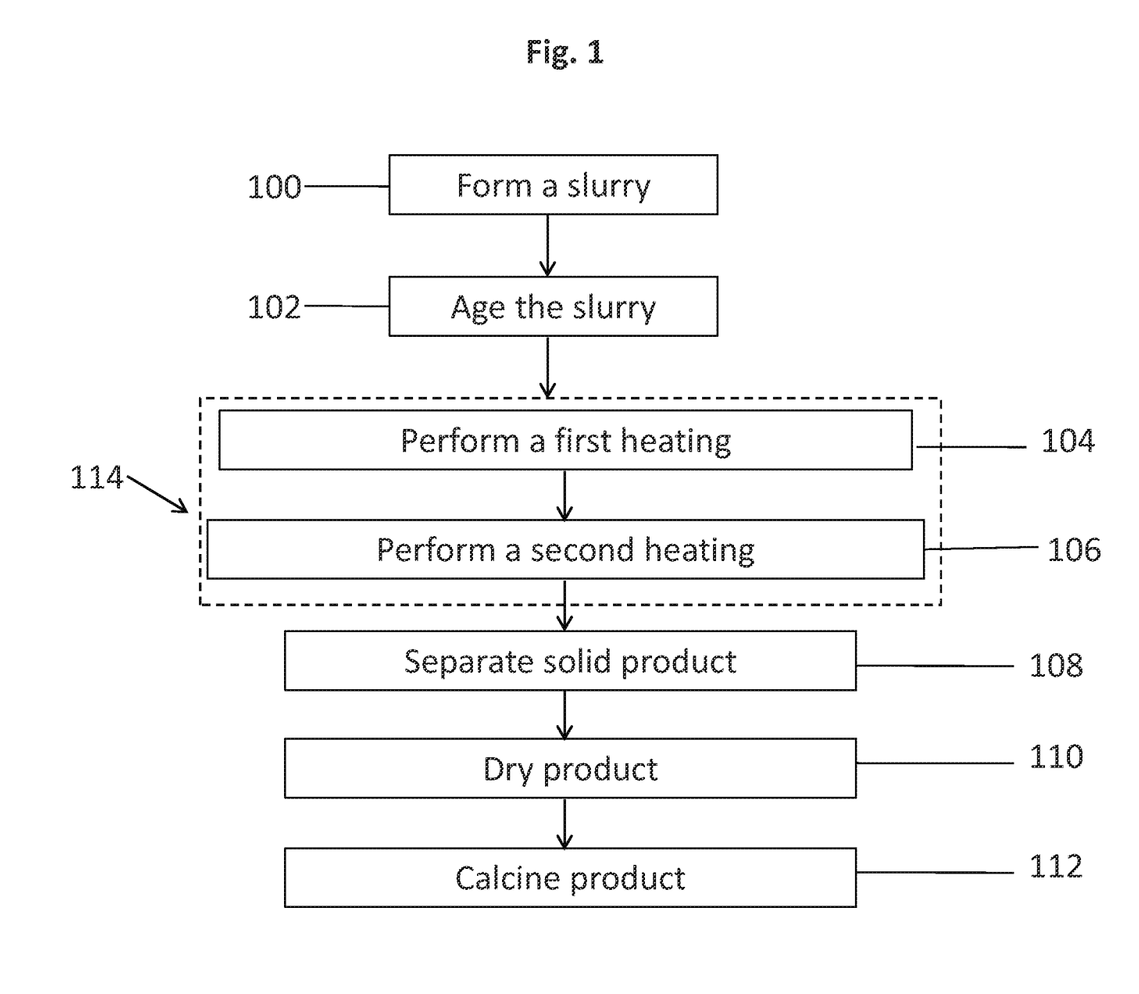
FIG. 1 shows a method for synthesizing silicoaluminophosphate-34 (SAPO-34) molecular sieves in accordance with one embodiment of the present invention.

FIG. 1 shows a method for synthesizing silicoaluminophosphate-34 (SAPO-34) molecular sieves in accordance with one embodiment of the present invention. The method includes first forming a slurry comprising monoisopropanolamine. The slurry may include a source of phosphorus, a source of aluminium, and a source of silicon. Then, the slurry is aged to form an aged slurry. Finally, crystallization of SAPO molecular sieves comprising the SAPO-34 molecular sieves is induced from the aged slurry.

Non-limiting examples of suitable sources of phosphorous, which may also include aluminium-containing phosphorus compositions, include phosphoric acid, organic phosphates such as triethylphosphate, phosphate salts such as ammonium phosphate, tretraethylammonium phosphate, and crystalline or amorphous aluminophosphates such as $AlPO_4$, phosphorus salts, or any combinations thereof. A preferred source of phosphorus is phosphoric acid.

Non-limiting examples of suitable sources of aluminium include organoaluminium compounds such as aluminium alkoxides and inorganic aluminium sources such as aluminium phosphate, aluminium hydroxide, sodium aluminate, boehmite, pseudo-boehmite, gibbsite and aluminium trichloride, or any combination thereof. A preferred source of aluminium is pseudo-boehmite.

Non-limiting examples of suitable sources of silicon include alkali silicate such as sodium silicate, fumed silica, organosilicon compounds such as tetraalkylorthosilicates, for example, tetramethylorthosilicate (TMOS) and tetraethylorthosilicate (TEOS), colloidal silicas or aqueous suspensions thereof, and silicic acid or any combination thereof. A preferred source of silicon is colloidal silica.

As shown in FIG. 1, the synthesizing method includes a forming step 100. At forming step 100, a slurry comprising monoisopropanolamine is formed. The slurry may include a source of phosphorus, a source of aluminium, and a source of silicon. The slurry may further include one or more other structure directing agents other than monoisopropanolamine. In one embodiment, the amounts of various components added into the slurry are determined according to the molar ratios shown in the following formula, i.e., $aR.bSiO_2.Al_2O_3.cP_2O_5.dH_2O$ (Formula 1), wherein R is monoisopropanolamine alone or a mixture with other structure directing agents, a is the molar ratio of organic structure directing agent or agents to $Al_2O_3$ and varies in the range of 0.1-4.0, b is the molar ratio of $SiO_2$ to $Al_2O_3$ and varies in the range of 0.02-2.0, c is the molar ratio of $P_2O_5$ to $Al_2O_3$ and varies in the range of 0.2-2.0, and d is the molar ratio of $H_2O$ to $Al_2O_3$ and varies in the range of 10 to 100. In the case that monoisopropanolamine is combined with other organic structure directing agent(s), the molar percentage of monoisopropanolamine over the total organic structure directing agents may range from 1% to 99%. In one embodiment, the molar ratio of monoisopropanolamine to $Al_2O_3$ may range from about 0.1 to about 3.0.

At forming step 100, the order of adding the starting components may vary, and the rates of adding the starting components may be 5 g or greater per minute. In one embodiment, the slurry is formed by first combining a source of phosphorus and water to form a phosphoric solution, to which a source of aluminium is introduced. Then, after the introduction of the source of aluminium, a source of silicon is introduced into the phosphoric solution. Finally, after the introduction of the source of silicon, monoisopropanolamine is introduced into the phosphoric solution to form a slurry. During and after the addition of the starting components, the slurry may be optionally mixed or agitated. The mixing of components may be performed at a temperature ranging from 10° C. to 100° C.

In another embodiment, the slurry is formed by first combining a source of phosphorus and water to form a phosphoric solution, to which a source of aluminium is introduced. Then, after the introduction of the source of aluminium, a source of silicon is introduced into the phosphoric solution. Finally, after the introduction of the source of silicon, monoisopropanolamine in conjunction with one or more other organic structure directing agent(s) is introduced into the phosphoric solution to form a slurry. Monoisopropanolamine and other organic structure directing agent(s) can be added to the aluminium, phosphorus and silicon containing slurry individually or in a form of a pre-mixed template mixture or mixture solution comprising monoisopropanolamine and other organic structure directing agents.

Non-limiting examples of suitable other structure directing agents include tetraalkyl ammonium compounds and amines including salts and substituted alkyl group connecting to nitrogen thereof, such as tetramethyl ammonium compounds, tetraethyl ammonium compounds, tetrapropyl ammonium compounds, and tetrabutylammonium compounds, cyclohexylamine, morpholine, propylamine, di-n-propylamine (DPA), tripropylamine, diethylamine (DEA), triethylamine (TEA), ethanolamine, N,N-diethanolamine, N,N-diethylethanolamine, diisopropanolamine, triisopropanolamine, N,N-dimethyl ethanolamine, N-methylethanolamine, N-methyldiethanolamine, triethanolamine, methanolamine, dimethanolamine, trimethanolamine, piperidine, cyclohexylamine, 2-methylpyridine, N,N-dimethylbenzylamine, dicyclohexylamine, choline, N,N'-dimethylpiperazine, N',N',N,N-tetramethyl-(1,6)hexanediamine, N-methyl piperidine, 3-methyl-piperidine, N-methyl cyclohexylamine, 3-methylpyridine, 4-methyl-pyridine, quinuclidine, di-n-butylamine, neopentylamine, di-n-pentylamine, isopropylamine, diisopropylamine, t-butylamine, ethylenediamine, pyrrolidine, 2-imidazolidone and diglycolamine. Preferred other structure directing agents are tetraethylammonium hydroxide, morpholine, diethylamine and triethylamine.

After forming step 100 is completed, the method continues to aging step 102.

At aging step 102, the slurry is aged. The slurry may be aged at a temperature ranging from about 10° C. to about 170° C., preferably from about 20° C. to about 150° C., for any period of time longer than 0.5 hours, preferably from about 0.5 hour to about 72 hours, and more preferably from 1 hour to 30 hours. Other methods of aging or assisting in the aging of the slurry include mechanical agitation, and/or milling, and/or sonication.

Without being held to a particular theory, it is believed that at forming step 100 and aging step 102, silicon, aluminium, and phosphorus sources disassociate from their respective original forms, and these dissociated species are rearranged to form Al—O—P—O and/or Si—O—Al—O—P—O linkages. No SAPO-34 crystalline phase is detected under X-Ray Diffraction at these steps.

After aging step 102 is completed, the method continues to inducing crystallization step 114.

At inducing crystallization step 114, crystallization of SAPO molecular sieves comprising the SAPO-34 molecular sieves is induced from the aged slurry. In one embodiment of the invention, crystallization is induced by a heating protocol using two steps, i.e., a first heating step 104 and a second heating or crystallization step 106.

At first heating step 104, the slurry is additionally aged under a high temperature to ensure the formation and mixing of the crystal nuclei precursors, nuclei and/or crystallites throughout the entire slurry. In one embodiment, the aged slurry is initially heated to a first temperature ranging from about 50° C. to about 170° C., preferably from about 80° C. to about 150° C., and then held at the first temperature for a time ranging from about 0.5 hour to about 24 hours, preferably from about 1 hour to about 10 hours. It is believed that this further maturation via first heating step 104 induces the formation of uniform crystals. After first heating step 104 is completed, the method continues to crystallization step 106.

At crystallization step 106, the slurry is further heated to a second temperature and held at the second temperature for a certain amount of time. In one embodiment, the slurry is further heated to a second temperature ranging from about 150° C. to about 250° C., preferably from about 170° C. to about 220° C., and then held at the second temperature for a time ranging from about 1 hour to about 100 hours, and preferably from about 5 hour to about 72 hours. In general, this second temperature should be higher than the first temperature at first heating step 104.

Without being held to a particular theory, it is believed that at crystallization step 106, amorphous phase and/or other precursory phase(s) transfer into SAPO-34 structure, and crystals grow to certain size. In one embodiment, the average diameter of SAPO-34 crystals is smaller than 10 µm, and the silicon ratio of SAPO-34 crystals is within the range from about 0.01 to about 0.3, and preferably from about 0.03 to about 0.2.

Another embodiment of inducing crystallization step 114 may include a single heating step protocol, in which the aged slurry is heated to a temperature that is the same as the second temperature at crystallization step 106, but at a heating rate not faster than 20° C. per minute. In one embodiment, the aged slurry is heated to a temperature within the range from about 150° C. to about 250° C., preferably from about 170° C. to about 220° C., and then holding the slurry at the temperature for a time within the range from about 1 hour to about 100 hours, preferably from about 5 hours to 72 hours. After inducing crystallization step 120 is completed, the method continues to separating step 108.

At separating step 108, SAPO molecular sieves comprising the SAPO-34 molecular sieves are recovered from the product slurry. Separating step 108 may include separation of the SAPO solids from the product slurry and washing of the SAPO solids. Non-limiting examples of separation equipments include vacuum filtration using filter cloth or paper, filter belts, filter presses, centrifuges, and/or membrane filters. Separating step 108 may be performed at a temperature ranging from 10 to 100° C., and preferably from room temperature to 70° C. In one embodiment, the solid SAPO molecular sieves may be separated by a filtration step through filters such as belt filters, filter presses, and membrane filters, and/or through centrifuges. The separated solid SAPO molecular sieves are then washed by water. The washing may be performed using separation equipment described above with the temperature of the washing water ranging from 10 to 100° C., and preferably from room temperature to 70° C. The purpose of the washing is to remove the residual compounds/salts from the recovered SAPO solids. The number of washing steps and the amount and pH of washing water are adjusted to ensure that the recovered SAPO solids are devoid of any impurities. For example, if sodium silicate is used as a silicon precursor, it may be advantageous to acidify the washing water or ammonium salt solution such as ammonium sulfate, chloride and phosphate to remove the residual sodium impurity from the recovered SAPO solids. After separating step 108, the solid SAPO molecular sieves are collected. The water content in the solid SAPO molecular sieves may be less than 80% by weight, and preferably less than 60% by weight. After separating step 108 is completed, the method continues to drying step 110.

At drying step 110, the SAPO molecular sieves comprising the SAPO-34 molecular sieves are dried to become free flowing powders. In one embodiment, the SAPO molecular sieves comprising the SAPO-34 molecular sieves are dried in a static oven, flash dryer, and/or tumbling dryer at a temperature ranging from 50° C. to 250° C., and preferably from 80° C. to 150° C. under the atmospheric condition or a flow of gas such as air. The water content in the SAPO molecular sieves after drying step 110 may be less than 20%, and preferably less than 10%.

After drying step 110 is completed, the SAPO-34 molecular sieves may have a chemical composition described on an anhydrous basis as $mR:(Si_x.Al_y P_z)O_2$ wherein m is in the range of 0.02 to 0.2, x in the range of 0.01 to 0.3, y in the range of 0.3 to 0.6, and z in the range of 0.3 to 0.6. After drying step 110 is completed, the method continues to calcining step 112.

At calcining step 112, the SAPO molecular sieves comprising the SAPO-34 molecular sieves are calcined to remove or burn off the residual organic structure directing agent or agents. The SAPO molecular sieves comprising the SAPO-34 molecular sieves may be calcined in a static furnace, moving bed furnace and/or rotary calciner at a temperature ranging from 350° C. to 950° C. under the atmospheric condition or a flow of gas such as air, oxygen, or nitrogen. Air is preferred. The calcination conditions are adjusted in a manner such that the total carbon left behind from the residual organic structure directing agent or agents in the calcined solid product may be not more than 5%, and preferably not more than 1%. The total weight loss of the calcined solid product may be not more than 15%, and preferably not more than 10% at 850° C. for 5 hours.

The SAPO molecular sieves comprising the SAPO-34 molecular sieves from separating step 108, drying step 110 and/or calcining step 112 may be further combined with formulating agents such as a matrix material and a binding agent to form catalyst particles. In one embodiment, the SAPO molecular sieves used to make catalyst particles comprise one or more metal elements from groups 1 to 14 such as transition metal elements. The metal elements may be incorporated by introducing metal containing compounds such as metal salts or/and hydroxides to the slurry during forming step 100 or aging step 102. In another embodiment, metal containing compounds may be introduced into SAPO molecular sieves after crystallization step 106 through physical mixing, ion-exchange, and/or impregnation.

The particle size of these catalyst particles may be in a range from 10 microns to 5 millimeters depending on the type of reactor operation. For example, for a fluidized bed reactor, an average particle size from 10-150 microns, preferably from 50-100 microns, is suitable. For a fixed bed operation, an average particle size from 1 mm-5 mm, preferably from 1.5-3 mm, is suitable.

The weight percentage of the SAPO molecular sieves comprising the SAPO-34 molecular sieves on a dry basis in the catalyst particles may be from 20 to 90%. The matrix material is preferably selected from clays such as kaolin, with a weight percentage ranging from 20 to 90% in the catalyst particles. The matrix material may be one or a combination of two or more materials. The matrix material typically plays the role of a filler to reduce cost and/or control diffusion of reactants and products throughout the catalyst particles.

The binding agents may comprise aluminium based or silicon based binders. Non-limiting examples of binding agents include aluminium nitrate, aluminium chloride, aluminium chlorohydrol, aluminium sulphate, aluminium phosphate, peptized alumina, peptized aluminium hydroxide, alumina sol, silica sol, and any combination thereof, with a weight percentage ranging from 5% to 30% in the catalyst particles. The binding agent is used to bind catalytically active component such as SAPO-34 in this invention with the matrix material such as clays to form shaped particles with desirable strength.

The SAPO molecular sieves comprising the SAPO-34 molecular sieves and the formulating agents may be mixed with or without mechanical grinding, and the mixture is then converted into particles of desirable size and shape, followed by a calcination step at a temperature ranging from 200° C. to 950° C. for a time ranging from 1 hour to 10 hours under the atmospheric condition or a flow of gas such as air. In one embodiment, the mixture is spray dried to form spherical particles with an average size ranging from 10 to 200 μm, and preferably from 50 to 100 μm.

The formulated catalyst may be used in the conversion of light oxygenates to light olefins. The light oxygenate feedstocks include alcohols, aldehydes, ketones, ethers, or mixtures thereof, and more preferably light alcohols and ethers containing 1-6 carbon atoms. It is particularly advantageous to use SAPO-34 of high structural purity, as disclosed herein, for the conversion of methanol to olefins (MTO) as described by Kaiser (U.S. Pat. No. 4,499,327).

Hereinafter, the present invention will be described in more detail with reference to Examples. However, the scope of the present invention is not limited to the following examples.

EXPERIMENTS

Structure is measured by X-Ray Diffractometer (PRO MPD from PANalytical) with voltage of 45 kV and current of 40 mA, using Cu-target at λ=1.54 Å. The samples for all XRD measurement are prepared by drying 5 grams of solid products obtained from separating step 108 during the synthesis at 120° C. for 5 hours. The dried solid products are further crushed into powders if necessary for XRD measurement. Crystal size is measured under SEM, where two areas of samples are randomly selected and imaged under various magnifications. The average of diameters of forty SAPO-34 crystals, twenty in each selected area, is taken. Molar ratio of Si/(Si+Al+P) is calculated from $SiO_2$%, $Al_2O_3$% and $P_2O_5$% by weight which are analyzed by Inductively Coupled Plasma method.

Example 1

5.2 g of 85% phosphoric acid $(H_3PO_4)_a$nd 15.7 g of $H_2O$ were combined to form a diluted $H_3PO_4$ solution. Then, 3.0 g of Catapal® B alumina was added under agitation to the diluted $H_3PO_4$ solution to form a homogeneous mixture. After the addition of Catapal® B was completed, 2.7 g of Ludox® AS-30 colloidal silica (30 wt. % of $SiO_2$) was added into the mixture under agitation until the mixture became homogeneous. Finally, after the addition of Ludox® AS-30 was completed, 3.4 g of monoisopropanolamine (MiPA) was added under agitation to form a slurry. The slurry was further stirred at room temperature for about 24 hours to obtain an aged slurry. The composition of the initial gel was as follows:

2.0MiPA:0.6SiO$_2$:1.0Al$_2$O$_3$:1.0P$_2$O$_5$:50H$_2$O

The gel was transferred into a Teflon-lined stainless steel autoclave, and heated to a temperature of 120° C. and held at the temperature of 120° C. for 5 hours, and then was further heated to a temperature of 200° C. and held at the temperature of 200° C. for 60 hours under autogenous pressure. The obtained solid product was centrifuged, washed, dried and calcined. The major XRD peaks of the dried product are shown in Table 1, indicating a SAPO-34 structure. The final product on anhydrous basis showed the following composition: $Si_{0.15}Al_{0.48}P_{0.37}O_2$.

TABLE 1

| 2θ, degree | d-spacing, Å | Relative Intensity, % |
|---|---|---|
| 9.49 | 9.32 | 100 |
| 12.87 | 6.88 | 25.41 |
| 16.01 | 5.54 | 34.98 |
| 17.75 | 5.00 | 18.34 |
| 20.59 | 4.31 | 99.79 |
| 21.98 | 4.04 | 10.73 |
| 23.04 | 3.86 | 14.36 |
| 24.90 | 3.58 | 47.11 |
| 25.90 | 3.44 | 17.35 |
| 30.58 | 2.92 | 39.74 |
| 31.03 | 2.88 | 21.36 |
| 34.46 | 2.60 | 6.8 |
| 35.96 | 2.50 | 5.4 |

Example 2

The synthesis was conducted in the same fashion as Example 1 except using less Ludox As-30 to make the initial gel. The composition of the initial gel was shown as follows:

2.0MiPA:0.2SiO$_2$:1.0Al$_2$O$_3$:1.0P$_2$O$_5$:50H$_2$O

After crystallization, the resultant product showed the same XRD characteristic peaks as those in Table 1. The final product on anhydrous basis showed the following composition: $Si_{0.01}Al_{0.48}P_{0.48}O_2$.

Example 3

118.1 g of 85% phosphoric acid (H$_3$PO$_4$) and 238.7 g of H$_2$O were combined to form a diluted H$_3$PO$_3$ solution. Then, 68.2 g of Catapal® B alumina was added under agitation to the diluted H$_3$PO$_4$ solution to form a homogeneous mixture. After the addition of Catapal® B was completed, 61.9 g of Ludox® AS-30 colloidal silica (30 wt. % of SiO$_2$) was added into the mixture under agitation until the mixture became homogeneous. Finally, after the addition of Ludox® AS-30 was completed, a premixed solution containing 69.7.1 g of MiPA and 43.4 g of 35%0 of tetraethylammonium hydroxide (TEAOH) was added under agitation to form a slurry. The slurry was further stirred at room temperature for about 24 hours to obtain an aged slurry. The molar ratio of the initial gel was as follows:

1.8MiPA:0.2TEAOH:0.6SiO$_2$:1.0Al$_2$O$_3$:1.0P$_2$O$_5$:40H$_2$O

Figure 2A:
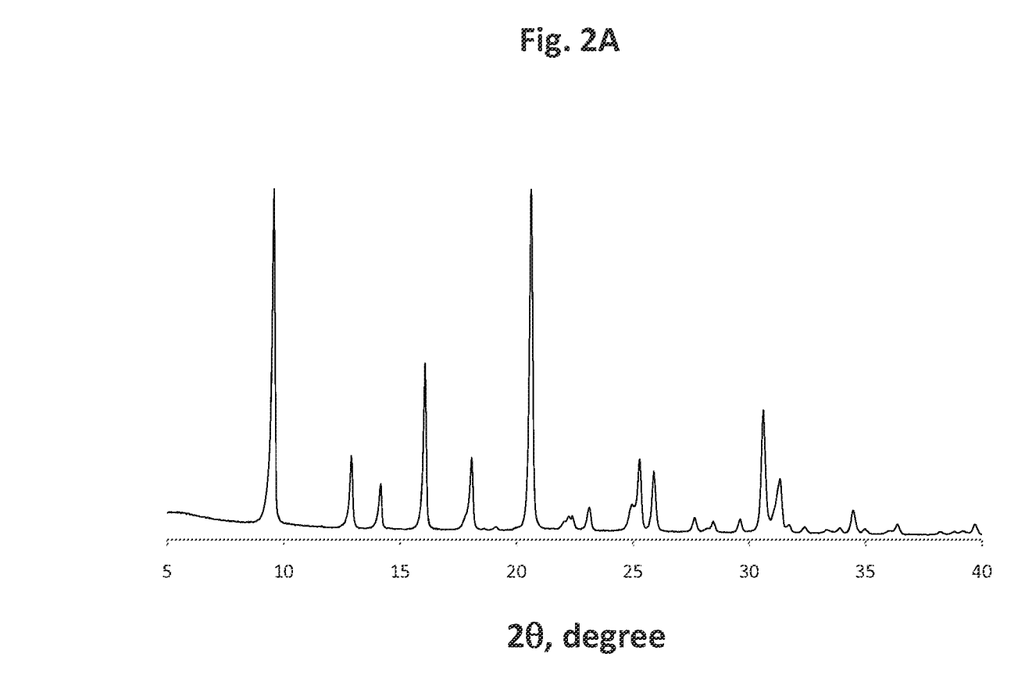
FIGS. 2A and 2B show a typical x-ray diffraction (XRD) pattern and a SEM image of the solid products obtained from Example 3 of the present application, respectively.
Figure 2B:
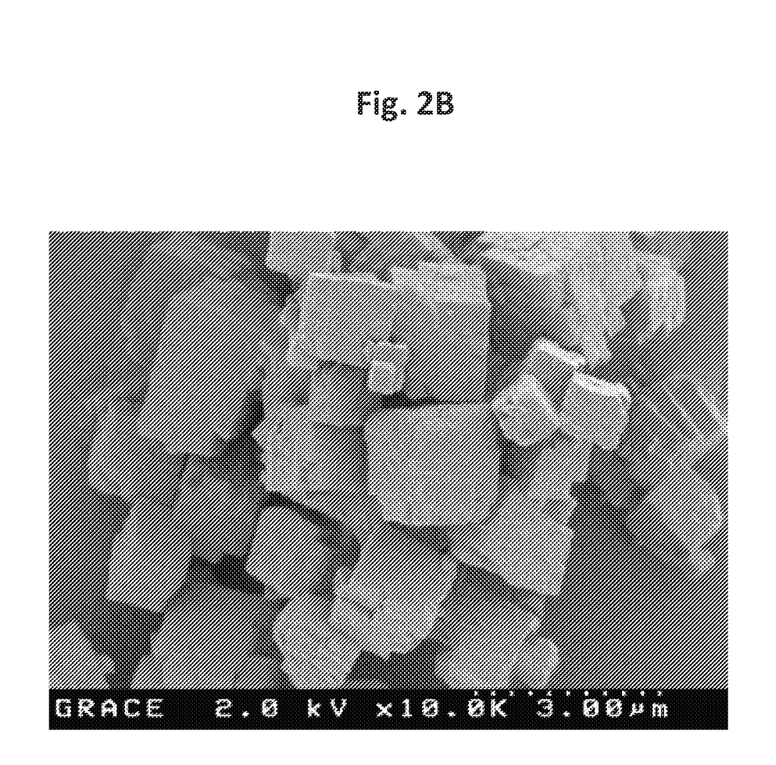

The above aged slurry was transferred to a 1 L autoclave with an agitation rate of at least 100 rpm. The mixture of aged slurries was initially heated to a temperature of 150° C. and held at the temperature of 150° C. for 2 hours under autogenous pressure. Then, the mixture of aged slurries was further heated to a temperature of 190° C. and held at the temperature of 190° C. for 16 hours under autogenous pressure. The obtained solid product was filtered, washed, dried, and calcined. FIGS. 2A and 2B show a typical x-ray diffraction (XRD) pattern and a SEM image of the solid products obtained, respectively. The major XRD peaks of the dried product are shown in Table 2, indicating a SAPO-34 structure. The composition of the final product on anhydrous basis was as follows: $Si_{0.18}Al_{0.46}P_{0.35}O_2$.

TABLE 2

| 2θ, degree | d-spacing, Å | Relative Intensity, % |
|---|---|---|
| 9.58 | 9.23 | 92.48 |
| 12.91 | 6.86 | 20.86 |
| 14.16 | 6.25 | 12.27 |
| 16.07 | 5.51 | 46.5 |
| 18.08 | 4.91 | 20.87 |
| 20.64 | 4.30 | 100 |
| 23.13 | 3.84 | 6.42 |
| 24.92 | 3.57 | 6.59 |
| 25.30 | 3.52 | 19.9 |
| 25.91 | 3.44 | 17.1 |
| 30.61 | 2.92 | 34.5 |
| 31.34 | 2.85 | 14.9 |
| 34.46 | 2.60 | 6.46 |

Example 4

The synthesis was conducted in the same fashion as Example 3 except that initial gel composition was different. The composition of the initial gel was shown as follows:

1.6MiPA:0.4TEAOH:0.2SiO$_2$:1.0Al$_2$O$_3$:1.0P$_2$O$_5$:40H$_2$O

After crystallization, the resultant product showed the same XRD characteristic peaks as those in Table 2. The final product on anhydrous basis showed the following composition: $Si_{0.08}Al_{0.50}P_{0.42}O_2$ Example 5

5.8 g of 85% phosphoric acid (H$_3$PO$_4$) and 10.3 g of H$_2$O were combined to form a diluted H$_3$PO$_4$ solution. Then, 3.3 g of Catapal® B alumina was added under agitation to the diluted H$_3$PO$_4$ solution to form a homogeneous mixture. After the addition of Catapal® B was completed, 1.0 g of Ludox® AS-30 colloidal silica (30 wt, % of SiO$_2$) was added into the mixture under agitation until the mixture became homogeneous. Finally, after the addition of Ludox® AS-30 was completed, a mixture of 1.1 g of MiPA, 2.1 g of diethanolamine (DEtA) and 6.3 g of 35% TEAOH solution was added under agitation to form a slurry. The slurry was further stirred at room temperature for about 24 hours to obtain an aged slurry. The molar ratio of the initial gel was as follows:

0.6MiPA:0.8DEtA:0.6TEAOH:0.2SiO$_2$:1.0Al$_2$O$_3$:1.0P$_2$O$_5$:40H$_2$O

The gel was transferred into a Teflon-lined stainless steel autoclave, and heated to a temperature of 120° C. and held at the temperature of 120° C. for 5 hours, and then was further heated to a temperature of 200° C. and held at the temperature of 200° C. for 60 hours under autogenous pressure. The obtained solid product was centrifuged, washed, dried and calcined. After crystallization, the resultant product showed the same XRD characteristic peaks as those in Table 2.

Example 6

118.9 g of 85% phosphoric acid (H$_3$PO$_4$) and 268.6 g of H$_2$O were combined to form a diluted H$_3$PO$_4$ solution. Then, 68.6 g of Catapal® B alumina was added under agitation to the diluted $H_3PO_4$ solution to form a homogeneous mixture. After the addition of Catapal® B was completed, 62.3 g of Ludox® AS-30 colloidal silica (30 wt. % of $SiO_2$) was added into the mixture under agitation until the mixture became homogeneous. Finally, after the addition of Ludox® AS-30 was completed, a mixture of 54.5 g of MiPA and 27.1 g of morpholine was added under agitation to form a slurry. The slurry was further stirred at room temperature for about 24 hours to obtain an aged slurry. The molar ratio of the initial gel was as follows:

1.4MiPA:0.6morpholine:0.6$SiO_2$:1.0$Al_2O_3$:1.0$P_2O_5$: 40$H_2O$

The gel was transferred into a Teflon-lined stainless steel autoclave, and heated to a temperature of 150° C. and held at the temperature of 150° C. for 2 hours, and then was further heated to a temperature of 190° C. and held at the temperature of 190° C. for 16 hours under autogenous pressure. The obtained solid product was centrifuged, washed, dried and calcined. The dried product showed a SAPO-34 structure from the XRD measurement. The composition of the final product on anhydrous basis was as follows: $Si_{0.18}Al_{0.47}P_{0.35}O_2$.

Example 7

58 g of 85% phosphoric acid ($H_3PO_4$) and 9.9 g of $H_2O$ were combined to form a diluted $H_3PO_4$ solution. Then, 3.3 g of Catapal® B alumina was added under agitation to the diluted $H_3PO_4$ solution to form a homogeneous mixture. After the addition of Catapal® B was completed, 1.0 g of Ludox® AS-30 colloidal silica (30 wt. % of $SiO_2$) was added into the mixture under agitation until the mixture became homogeneous. After the addition of Ludox® AS-30 was completed, a premixed solution containing 3.0 g of MiPA and 6.3 g of TEAOH solution was added under agitation to form a slurry. Finally, 0.6 g of 40% of $HPF_6$ solution was added to the above slurry. The slurry was further stirred at room temperature for about 24 hours to obtain an aged slurry. The molar ratio of the initial gel was as follows:

1.6MiPA:0.6TEAOH:0.2$SiO_2$:1.0$Al_2O_3$:1.0$P_2O_5$: 0.07$HPF_6$:40$H_2O$

The gel was transferred into a Teflon-lined stainless steel autoclave, and heated to a temperature of 120° C. and held at the temperature of 120° C. for 5 hours, and then was further heated to a temperature of 200° C. and held at the temperature of 200° C. for 30 hours under autogenous pressure. The obtained solid product was centrifuged, washed, dried and calcined. The calcined product showed a SAPO-34 structure from the XRD) measurement. The composition of the calcined product on anhydrous basis was as follows: $Si_{0.06}Al_{0.51}P_{0.43}O_2$.

Comparative Example 1

The synthesis was conducted in the same fashion as Example 1 except using diethanolamine (DEtA) instead of isopropanolamine (MiPA) as template to make the initial gel. The composition of the initial gel was shown as follows:

2.0DEtA:0.6$SiO_2$:1.0$Al_2O_3$:1.0$P_2O_5$:50$H_2O$

After crystallization, the resultant product showed major XRD peaks at two theta 7.52°, 19.82°, 21.03° and 22.46°, indicating the product was mainly SAPO-5.

Comparative Example 2

The synthesis was conducted in the same fashion as Example 1 except using diisopropanolamine (DiPA) instead of isopropanolamine (MiPA) as template to make the initial gel. The composition of the initial gel was shown as follows:

2.0DiPA:0.6$SiO_2$:1.0$Al_2O_3$:1.0$P_2O_5$:50$H_2O$

Figure 3:
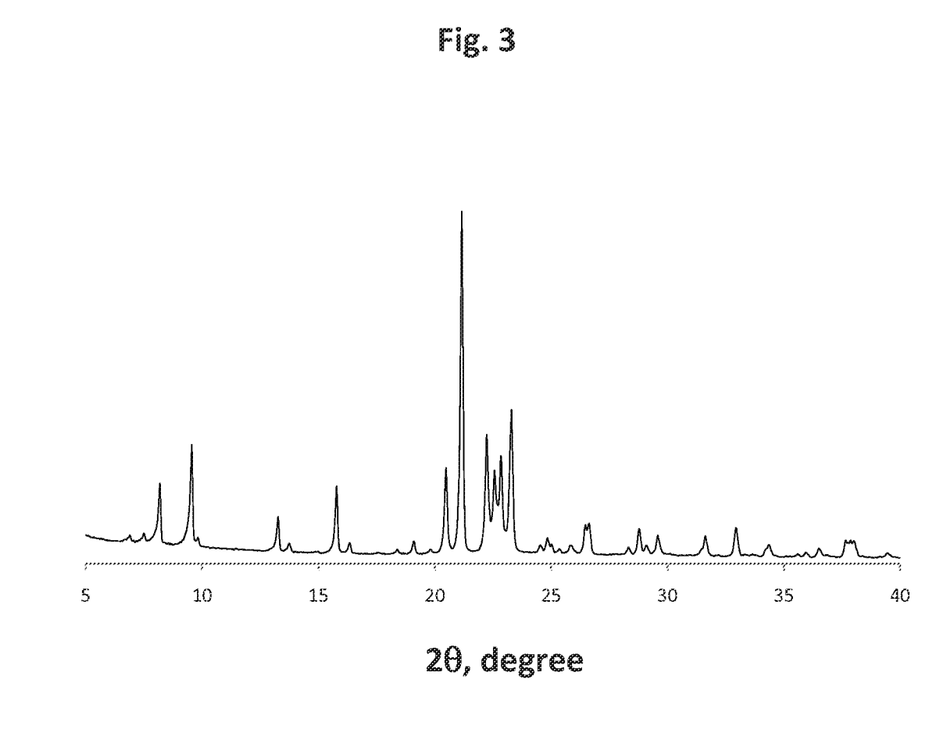
FIG. 3 shows an XRD pattern of the solid products obtained from Comparative Example 2 of the present application.

After crystallization, the resultant product showed a mixture of SAPO-34, SAPO-5 and unidentified impurity phase(s) with main XRD peaks at 2θ=8.16° and 21.13°. FIG. 3 shows an XRD pattern of the solid products obtained.

Comparative Example 3

The synthesis was conducted in the same fashion as Example 3 except using diethanolamine (DEtA) instead of isopropanolamine (MiPA) as template to make the initial gel. The composition of the initial gel was shown as follows:

1.6DEtA:0.4TEAOH:0.6$SiO_2$:1.0$Al_2O_3$:1.0$P_2O_5$:40$H_2O$

After crystallization, the resultant product showed a mixture of SAPO-34 and SAPO-5 from the XRD measurement.

The invention claimed is:

1. A method for synthesizing silicoaluminophosphate-34 (SAPO-34) molecular sieves, comprising:
    forming a slurry comprising monoisopropanolamine, a source of phosphorus, a source of aluminium, and a source of silicon;
    aging the slurry to form an aged slurry; and
    inducing crystallization of silicoaluminophosphate molecular sieves comprising the SAPO-34 molecular sieves from the aged slurry.

2. The method of claim 1, wherein the molar ratio of monoisopropanolamine to $Al_2O_3$ ranges from about 0.1 to about 3.

3. The method of claim 1, wherein the slurry further comprises one or more other structure directing agents.

4. The method of claim 3, wherein the other structure directing agents are selected from the group consisting of tetraethylammonium hydroxide, morpholine, diethylamine, and triethylamine.

5. The method of claim 3, wherein the other organic structure directing agents comprise tetraethylammonium hydroxide.

6. The method of claim 3, wherein forming the slurry comprises:
    combining the source of phosphorus and water to form a phosphoric solution;
    introducing the source of aluminium into the phosphoric solution;
    introducing the source of silicon into the phosphoric solution after the introduction of the source of aluminium; and
    introducing monoisopropanolamine and one or more other structure directing agents into the phosphoric solution after the introduction of the source of silicon.

7. The method of claim 1, wherein forming the slurry comprises:
    combining the source of phosphorus and water to form a phosphoric solution;
    introducing the source of aluminium into the phosphoric solution;
    introducing the source of silicon into the phosphoric solution after the introduction of the source of aluminium; and
    introducing monoisopropanolamine into the phosphoric solution after the introduction of the source of silicon.

8. The method of claim 1, wherein aging the slurry is performed by aging the slurry at a temperature within the range from about 10° C. to about 170° C. for a time within the range from about 0.5 to 72 hours.

9. The method of claim 1, wherein aging the slurry is performed by aging the slurry at a temperature within the range from about 20° C. to about 150° C. for a time within the range from about 1 hour to about 30 hours.

10. The method of claim 1, wherein the inducing crystallization step comprises:
    initially heating the aged slurry to a first temperature within the range from about 50° C. to about 170° C. and then holding the slurry at the first temperature for a time within the range from about 0.5 hour to about 24 hours; and
    further heating the aged slurry to a second temperature within the range from about 150° C. to about 250° C. and then holding the slurry at the second temperature for a time within the range from about 1 hour to about 100 hours.

11. The method of claim 1, wherein the inducing crystallization step comprises:
    initially heating the aged slurry to a first temperature within the range from about 80° C. to about 150° C. and then holding the mixture at the first temperature for a time within the range from about 1 hour to about 10 hours; and
    further heating the aged slurry to a second temperature within the range from about 170° C. to about 220° C. and then holding the slurry at the second temperature for a time within the range from about 5 hour to about 72 hours.

12. The method of claim 1, wherein the inducing crystallization step comprises:
    heating the aged slurry to a temperature within the range from about 150° C. to about 250° C. and then holding the slurry at the temperature for a time within the range from about 1 hour to about 100 hours.

13. The method of claim 1, wherein the inducing crystallization step comprises:
    heating the aged slurry to a temperature within the range from about 170° C. to about 220° C. and then holding the slurry at the temperature for a time within the range from about 5 hour to about 72 hours.

14. The method of claim 1, wherein the silicoaluminophosphate molecular sieves have a silicon ratio of about 0.01 to about 0.3.

15. The method of claim 1, wherein the silicoaluminophosphate molecular sieves have a silicon ration of about 0.03 to about 0.2.

16. The method of claim 1, wherein the average diameter of the SAPO-34 molecular sieves is smaller than 10 μm.

* * * * *